(12) United States Patent
Martikka et al.

(10) Patent No.: US 9,616,291 B2
(45) Date of Patent: Apr. 11, 2017

(54) WEARABLE SPORTS MONITORING EQUIPMENT WITH CONTEXT DETERMINATION CAPABILITIES AND RELATING METHOD

(71) Applicant: Suunto Oy, Vantaa (FI)

(72) Inventors: Mikko Martikka, Vantaa (FI); Heikki Nieminen, Vantaa (FI); Kimmo Pernu, Vantaa (FI); Olli-Pekka Ojanen, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

(21) Appl. No.: 14/940,183

(22) Filed: Nov. 13, 2015

(65) Prior Publication Data

US 2016/0144235 A1 May 26, 2016

(30) Foreign Application Priority Data

Nov. 19, 2014 (FI) ..................................... 20146008
Nov. 19, 2014 (GB) ................................... 1420536.3

(51) Int. Cl.
  *A63B 24/00* (2006.01)
  *A61B 5/024* (2006.01)
  (Continued)

(52) U.S. Cl.
  CPC ...... *A63B 24/0062* (2013.01); *A61B 5/02438* (2013.01); *A61B 5/1118* (2013.01);
  (Continued)

(58) Field of Classification Search
  CPC ... A61B 5/1118; A61B 5/02438; A61B 5/222; A61B 5/6804; A61B 5/0402; A61B 5/6831; A63B 24/0062; A63B 2024/0071
  See application file for complete search history.

(56) References Cited

U.S. PATENT DOCUMENTS 9,089,285 B2 * 7/2015 Lee .................... A61B 5/222
2007/0051369 A1 3/2007 Choi et al.
(Continued)

FOREIGN PATENT DOCUMENTS

EP 2745777 A1 6/2014
WO WO2010084430 A1 7/2010
(Continued)

*Primary Examiner* — Jasson Yoo
(74) *Attorney, Agent, or Firm* — Seppo Laine Oy

(57) ABSTRACT

The invention relates to sports monitoring equipment and methods. The invention provides a device or system comprising means for reading a heartbeat signal corresponding to heartbeat of the person during the performance, and means for reading a motion signal corresponding to motion of the person during the performance. There are also computing means for estimating energy consumption of the person during the performance using one or both of said signals. According to the invention, the device or system further comprises means for determining the type of the sports performance. The computing means for calculating the energy consumption parameter are adapted to utilize said heartbeat signal, said motion signal or both signals in combination in a manner depending on the type of the sports performance determined. The invention allows for accurate estimation of energy consumption in versatile sports.

16 Claims, 7 Drawing Sheets

(51) Int. Cl.
  *A61B 5/22*    (2006.01)
  *A61B 5/11*    (2006.01)
  *A61B 5/0402*  (2006.01)
  *A61B 5/00*    (2006.01)

(52) U.S. Cl.
  CPC ............ *A61B 5/222* (2013.01); *A61B 5/0402* (2013.01); *A61B 5/6804* (2013.01); *A61B 5/6831* (2013.01); *A63B 2024/0071* (2013.01)

(56) References Cited

U.S. PATENT DOCUMENTS

| | | | |
|---|---|---|---|
| 2010/0256532 A1* | 10/2010 | Nishibayashi | A61B 5/1118 600/595 |
| 2010/0305480 A1 | 12/2010 | Fu et al. | |
| 2012/0083705 A1 | 4/2012 | Yuen et al. | |
| 2014/0213920 A1 | 7/2014 | Lee et al. | |
| 2015/0153374 A1* | 6/2015 | Balakrishnan | G01P 13/00 702/178 |

FOREIGN PATENT DOCUMENTS

| | | |
|---|---|---|
| WO | WO2012093397 A2 | 7/2012 |
| WO | WO2014120831 A1 | 8/2014 |

\* cited by examiner

WEARABLE SPORTS MONITORING EQUIPMENT WITH CONTEXT DETERMINATION CAPABILITIES AND RELATING METHOD

FIELD OF THE INVENTION

The invention relates to wearable electronic equipment for monitoring sports performances and related methods. In particular, the invention relates to a solution for determining energy consumption of a person during a performance. More specifically, the invention provides a device or multi-device system and a method for this purpose.

BACKGROUND OF THE INVENTION

Heart rate sensors are commonly used for monitoring and characterizing sports performances. Most commonly, they are based on electric measurement of heart activity using electrodes placed on the skin of a person, i.e. using an electrocardiographic (ECG) measurement. Heart rate can be determined by detecting individual heartbeats from the ECG signal and counting their frequency. Heart rate as such is an important characteristic parameter of the performance but it can also be used to estimate for example energy consumption of the person. This is also very common in existing sports monitoring equipment.

It has been found that in certain situations heart rate is not a good indicator of energy consumption and its use results in erroneous energy consumption values. Correction of energy consumption can be carried out to some extent using other data available, see for example FI Application No 20115150 or FI Application No 20105310, but even that does not result in satisfactory results in all cases. EP 1862117, on the other hand, discloses a method for calibrating calculation of energy consumption using activity data, in particular by taking into account the delay at which the heart rate follows the changes in activity level.

Determining energy consumption from heart rate is particularly challenging in low-intensity performances, i.e. when heart activity due to the physical performance is only slightly or moderately above the resting heart activity. The heart rate is influenced not only by the physical effort, but also by psychological factors and other factors stimulating the neural network, such as excitement, and error from such contributions is relatively high in low-intensity performances. There are no reliable methods available for taking such errors into account.

Energy consumption can also be determined by measuring or estimating ventilation during the performance, but that approach demands instrumentation which is impractical in training sessions. Alternatively, energy ventilation can be estimated based on inter-beat intervals of the ECG signal, see for example FI Application No 20086146, has a considerable source of error due to physiological constraints and measurement constraints.

Thus, there is a need for improved method for determining energy consumption in versatile training situations.

SUMMARY OF THE INVENTION

It is an aim of the invention to provide a solution for determining energy consumption during a physical exercise that suits for versatile training situations.

A further aim is to provide a method for characterizing a sports performance.

The invention is based on the perception that energy consumption is dependent on the context the measurement is carried out in, and most importantly the type of sports performed. Although heart rate gives a rough estimate on energy consumption in all situations, two different types of sports performances resulting in practically the same average heart rate level can cause or demand very different metabolic processes in the body and therefore consume very different amounts of energy. For example, in skiing, a particular heart rate can imply working at the aerobic range but in running, the same heart rate is in the anaerobic range.

The invention tackles this problem by providing a sports context intelligence into the monitoring equipment. In particular, the invention provides a device or system which is able to deduct the type of sports, herein called context, using measurements carried out during the performance and to choose the most suitable estimation method for energy consumption. For example, different sources of performance measurement data can be used depending on the context, or they may be weighed or used in different manner for different types of sports.

In still further details, the invention provides sports monitoring equipment comprising means for reading a heartbeat signal corresponding to heartbeat of the person during the performance, and means for reading a motion signal corresponding to motion of the person during the performance. There are also computing means for estimating energy consumption of the person during the performance using one or both of said signals. According to the invention, the equipment further comprises means for determining the type of the sports performance. The means for calculating the energy consumption parameter are adapted to utilize the heartbeat signal, the motion signal or both signals in combination in different manner depending on the type of the sports performance determined. The type of the sports performance can be determined either manually by the user but even more advantageously automatically, as will be describe later in more detail. The invention can take the form of a single device containing all functional parts or a multi-device system where the functionalities are distributed between two or more device units having a preferably wireless communication link between them.

The invention also provides a corresponding method for sports monitoring.

More specifically, the invention is characterized by what is stated in the independent claims.

The invention provides considerable advantages. The general advantage is that the operation of the equipment is adapted depending on the sports, i.e. context, the equipment is being used in. This allows for more reliable estimation of energy consumption, which—as discussed above—depends significantly on the nature of sports being done. The present solution suits particularly well for distinguishing between irregular and monotonic sports performances and their individual accurate characterization, accordingly.

The solution can be implemented in a computationally feasible manner in wearable devices.

In particular, by means of the invention it is possible to get a more accurate estimation for resting state energy consumption, which forms a basis for elevated-intensity estimation.

Also anaerobic heart rate threshold levels can be determined for each sports type separately and used to provide more accurate type-specific intensity or energy consumption estimates.

One advantage of the invention is that the energy consumption estimation can be reliably carried out even without using the results of heart rate measurement, provided that the determined type is such that its energy consumption is better characterized by the motion measurement.

According to one preferred embodiment, the invention solves the present problem by distinguishing the sports based on physical rhythmicity, i.e. similarity and temporal stability of successive similar movements, required in particular sports. For example, street or track running is physically very rhythmic sports, i.e. involves a stabile cadence, whereas tennis is more impulsive and irregular. The proposed solution can robustly distinguish between these kinds of sports and apply a corresponding algorithm for calculating energy consumption, which utilize at least partly different sources of information. Energy consumption of running may be better characterized by cadence and tennis by heart rate characteristics. Automatic type determination based on the stability of cadence is also capable of distinguishing between street or track running and cross county running or orienteering, which involve kinematically and/or temporally more versatile motion and in which energy consumption is usually better characterized by heart rate.

The dependent claims are directed to selected embodiments of the invention.

According to one embodiment, there are provided means for receiving and storing a user-specified sports performance type parameter in a memory of the equipment. This is called manual type determination. In addition, the means for determining the type of the sports performance are adapted to read said user-specified sports performance type parameter from said memory in order to determine the type of the sports performance. The means for receiving and storing may comprise user interface means and associated software and hardware means in a wristop computer or mobile phone part of the present system. If necessary, the performance type parameter can be communicated to a heart rate belt or some other unit where energy consumption calculations are carried out.

According to one embodiment, the equipment comprises a removable heartbeat and/or acceleration measurement module, which is capable of determining the type of sports based on an identification code read from the sports item, such as belt or smart garment, the module is mounted on.

According to one embodiment, the means for determining the type of the sports performance are adapted to determine the type of the sports performance automatically based on characteristics, in particular rhythmicity, of the motion signal. According to a further embodiment, this is implemented such that the means for determining the type of the sports performance are adapted to calculate a parameter depicting rhythmicity of the performance based on the motion signal and the device is adapted to use that parameter for determining the type. In one approach, the means for calculating the energy consumption parameter are adapted to utilize only the ECG signal in calculations if the rhythmicity of the performance is below a predefined level and only the motion signal if the rhythmicity of the performance is above the predefined level. Thus, rhythmic sports are characterized by the acceleration data, for example and irregular sports by the heart rate data, allowing for more accurate estimations for energy consumption.

According to one option, the means for determining the type of the sports performance are adapted to determine rhythmicity of the motion signal by detecting repeating features in the motion signal, associating time stamps to the repeating features, and calculating correlation between intervals between successive time stamps, preferably at all sensor axes. Correlation value per axis forms characterization vector that is utilized to differentiate between types of sports. Such correlation analysis can be implemented in a wearable device efficiently in the time domain.

In an alternative option, the means for determining the type of the sports performance are adapted to apply Fourier analysis on the motion signal to determine rhythmicity of the motion signal. Discrete Fourier analysis can also be relatively efficiently implemented in small devices, as disclosed in US 2012/215116, for example.

According to one embodiment, the means for reading the heartbeat signal comprise a heartbeat sensor, such as a pair of ECG electrodes adapted to be positioned against the chest of the person for providing the heartbeat signal. According to alternative embodiments, said means comprise an optical sensor, a pressure sensor or an acceleration sensor. Thus, instead of electrically detectable cardiographic response, the sensor may be sensitive for example to optically detectable cardiovascular changes due to heartbeats, cardiovascular pressure changes due to heartbeats or cardiovascular-induced motion detectable on the surface of skin.

The location of the heartbeat sensor during the performance may be the chest, waist, neck, wrist, upper arm or auricle, to mention some examples.

According to one embodiment, the means for reading the motion signal comprise a motion sensor, such as an acceleration sensor providing an acceleration signal as the motion signal. Acceleration sensors are particularly suitable for determining the cadence and rhythmicity of motion. An acceleration sensor placed in a device unit at the chest or other parts of the torso are particularly suitable. Alternatively or in addition to that, acceleration sensors placed in a device unit at a limb, such as wrist, foot or other parts of an arm or leg can be used. In one embodiment, at least two acceleration sensors are used in combination.

According to further embodiments, the motions sensor comprises a position sensor or a speed sensor, such as a satellite positioning sensor or velocimeter, such as a cyclometer, used for determining the speed of motion.

The means for calculating the energy consumption parameter and means for determining the type of sports performance may comprise a processing unit located in a single device unit or two or more separate processing units of different device units, depending on the overall equipment architecture. Examples of architecture include a single device unit being a heart rate measurement module part of or attachable to a garment or a wrist-worn unit comprising integrated sensors, and a distributed device model with two or more device units in wireless communication link with each other.

The processing unit(s) referred herein and contained in the one or more device units may comprise a data processor of any kind, in particular a microcontroller or a microprocessor together with potentially required related components, such as memory components (e.g. RAM, ROM) and input/output circuits functionally connected thereto. In the distributed device model, two or more processing units located in two or more device units and programmed to carry out different parts of the present method together form the means for calculating the energy consumption parameter and means determining the type of the performance.

According to one embodiment, the present equipment is an electronic module comprising an acceleration sensor integral or connectable with a heart rate belt or smart garment with ECG measurement electrodes for providing said ECG signal to the electronic module. According to a further embodiment, also the means for determining a type of the sports performance and optionally also the means for calculating the energy consumption parameter based on the ECG signal and/or motion signal, depending on the type of sports performance determined, are contained in said electronics module. There are also typically provided means for wirelessly communicating the energy consumption parameters to another electronic device. These embodiments deviate from the traditional model of sports monitoring systems, where the sensor modules lack the capability to perform significant computing tasks. The present heart rate module can be a combined heart rate and acceleration-sensing module with built-in sports type determination and even built-in energy consumption calculation.

According to one embodiment, the present system comprises, in addition to a heart rate (and optionally acceleration-sensing) module, a wristop computer or mobile phone. In this case, the means for reading the ECG signal (and optionally also said means for reading the motion signal) are adapted to receive the signal(s) wirelessly from the heart rate module.

The energy consumption parameter calculated in the invention can be for example energy consumption per mass unit, or the total energy consumption of the person. The former is particularly beneficial if the calculation is carried out in the heart rate module, since it does not require information about the mass of the person. Typically, cumulative consumptions for the performance are presented.

According to one embodiment, the present method comprises providing an ECG signal corresponding to the heartbeat of the person during the performance, providing a motion signal corresponding to the motion of the person during the performance, and calculating an energy consumption parameter using one or more of said signals. In addition, the method comprises determining a type of the sports performance and calculating the energy consumption parameter by utilizing said ECG signal, said motion signal or both signals in combination, in different manners depending on the type of the sports performance determined. According to one embodiment, the determination of the type of the sports performance is carried out on the basis of a sports type parameter specified by the user, i.e. the person to be monitored. The user can enter the sports type through a user interface of the monitoring equipment. According to another embodiment, the determination is carried out automatically based on the rhythmicity of the motion signal. According to an alternative and automatic sports type determination method, the method comprises calculating a rhythmicity parameter based on the motion signal, and using said motion signal for calculating the energy consumption parameter if the rhythmicity of the motion signal depicted by said rhythmicity parameter is above a predefined level, such as in street running or cycling, for example, and using said ECG signal for calculating the energy consumption parameter if the rhythmicity of the motion signal depicted by said rhythmicity parameter is below a predefined level, such as in indoor and/or team games or cross country running, for example.

DEFINITIONS

The term "type of sports performance" refers mainly to different sports necessitating different kinematic (motor) behavior, such as motor functions and/or temporal activity. In the simplest form of the invention, there are only two types that need to be distinguished: rhythmic (or cyclic) and non-rhythmic (with an irregular type of motion) sports. However, this separation can also be made finer. Thus, there may also be three or more types, for example intermediate types between and/or sub-types in each main type. The threshold(s) between the types need to be selected to correspond with the variety of sports the equipment is intended to be used in, also keeping an eye on the energy consumption algorithms chosen to be used. On a technical level, the type of the sports performance may be represented by a suitable computer-readable variable in a memory device. The type variable is configured to receive a value assigned to the type selected. Each sports type may thus have a unique value.

The terms "rhythmic" and "rhythmicity" refer to a behavior of movements and corresponding performance signals having a relatively constant frequency of successive motions with characteristic signal features. In other words, in "rhythmic" sports performance, similar body motions are repeated one after another at constant intervals. This results in a motion-sensitive signal where similar signal characteristics can be detected at constant intervals. In performances involving much irregular motion, either the body motions or their repetition intervals, typically both, are not similar from one to another. This results in a motion signal with more randomness. Rhythmicity can be characterized for the purposes of some embodiments of the invention using correlation or Fourier analysis, for example.

The term "wearable equipment" covers all mobile devices and multi-device systems, which are designed to or can otherwise be attached to one or more body parts directly or via a piece of clothing, including various kinds of shirts, jackets, pants and shoes, for example, or to a wearable accessory, such as a wearable mobile phone arm holder. Wearable devices include in particular wristop computers, mobile phones, heart rate belts, smart garments and sensor units of various kinds, such as ECG and EMG measurement modules, satellite positioning units, acceleration measurement units (foot and arm "pods"), providing some or all of the functionalities as herein described. In other words, the invention covers individual self-contained units providing the necessary functionalities of the invention and as well as systems formed of a plurality of separate units capable of communicating with each other so as to form an operational entity providing said functionalities.

Unless otherwise mentioned, references to a "heart rate belt" and "smart garment" include the option that the belt or garment contains, in addition to an integral heartbeat sensor, an integral computing and communication unit (hereinafter: processing unit) and the option that the processing unit is mountable to the belt or garment as a releasable module in functional connection with the heartbeat sensor. The term "module" may refer to an integral module in a heart rate belt or smart garment, or a removable module functionally connectable with a belt or garment.

"Reading" an (ECG or motion) signal covers direct measuring of the signal in a device but as well receiving the signal from another device over a wireless link, for example. As discussed above, the invention can be provided in the form of a system comprising one or more wearable sensor devices and a main processing unit in distributed configuration.

Next, embodiments and advantages of the invention are described in more detail with reference to the attached drawings.

DETAILED DESCRIPTION OF EMBODIMENTS

Figure 1A:
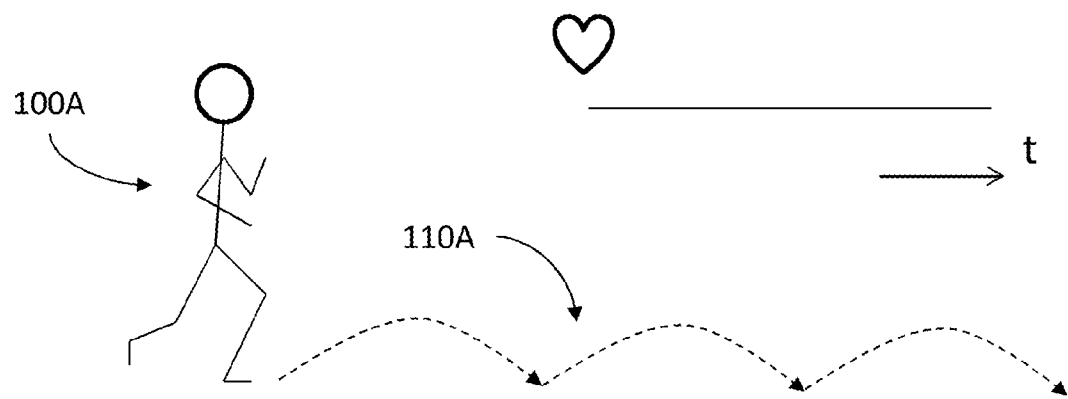
FIG. 1A shows an illustration of a sportsman doing rhythmic sports (running) and his heart rate vs. time behavior.
Figure 1B:
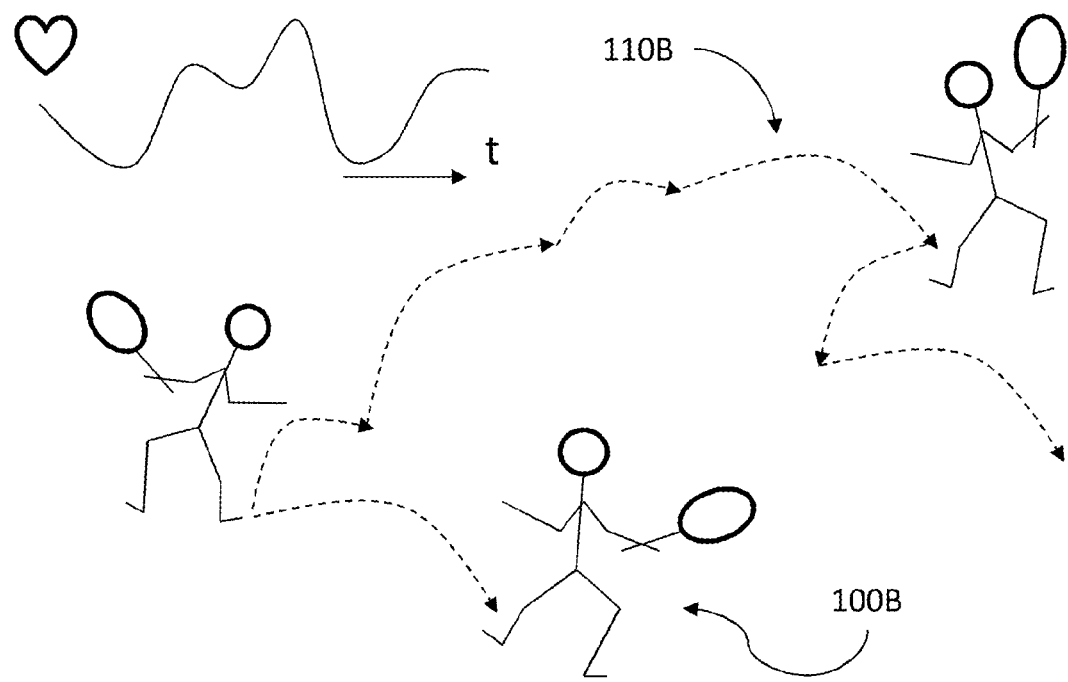
FIG. 1B shows an illustration of a sportsman doing irregular sports (tennis) and his heart rate vs. time behavior.

FIGS. 1A and 1B illustrate the problem setting that the invention tackles. In FIG. 1A, there is a runner 100A taking rhythmic steps 110A, i.e. moving forward with a stabile cadence. If the runner 100A keeps his pace constant, also his heart rate seeks towards and remains at a constant level over time, as shown in the related graph, or at least changes relatively slowly. FIG. 1B, on the other hand shows a more irregular movement 110B of a tennis player 100B, who during playing must make rapid changes of direction and speed and stop every now and then for shorter and longer periods (e.g. during pauses between points, games and sets). Thus, his cadence is irregular and overall physical strain very fluctuating, resulting in a heart rate diagram with large value range. No known energy consumption algorithm relying on a single source of performance data produces an accurate result in both of these two exemplary systems.

As referred to above, the present invention solves the problem by first determining the type of the sports performance, and then to utilize a different combination of heart rate and movement signals, depending on the type determined for calculating the desired performance parameter, most notably the energy consumption.

The following examples mostly illustrate a set-up with a heart rate belt and wristop computer. However, these devices can be replaced for example with a smart garment and/or mobile phone, in any suitable combination, without departing from the broadest scope of the invention.

Figure 2:
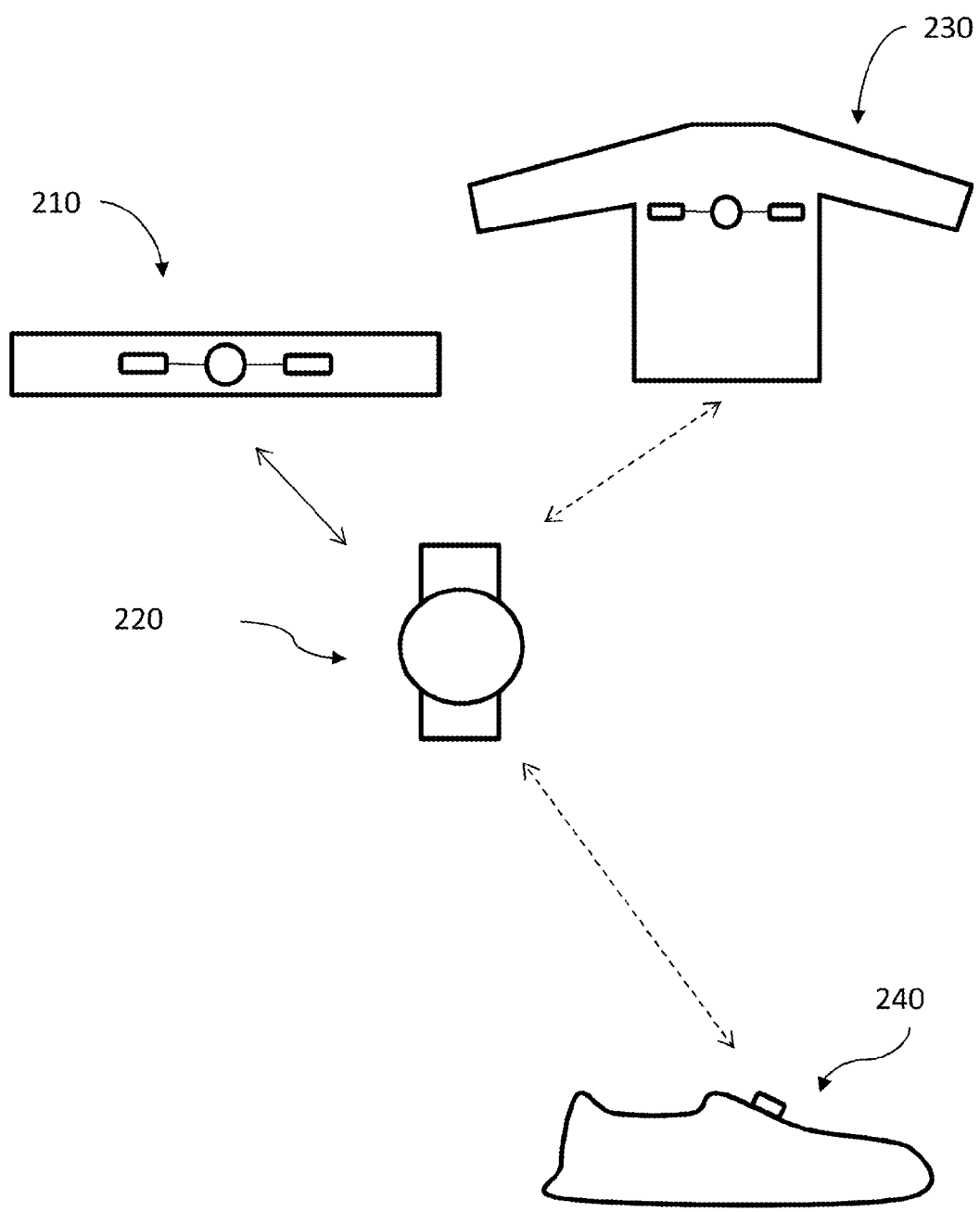
FIG. 2 shows a schematic view of a system according to one embodiment of the invention and some optional components and variations thereof.

FIG. 2 shows a system with a wristop computer 220 having a data storage and/or visualization device and a heart rate belt 210 acting as a data-collecting device. The heart rate belt comprises an ECG sensor and an electronic module that reads and processes the signal provided by the ECG sensor. An acceleration sensor is provided either in the heart rate belt 210 or the wristop computer 220, or both. The heart rate belt 210 is in wireless communication with the wristop computer.

As an alternative to a heart rate belt 210 a smart garment 230 can be used, providing the same functionality as the heart rate belt 210 discussed above.

In still a further embodiment, there may be provided as an additional unit in the equipment system a sensor unit attached to a shoe 240 of the sportsman. The additional sensor unit may comprise an acceleration sensor providing the acceleration signal and is in wireless communication with the heart rate belt 210 or smart garment 230 and/or the wristop computer 220, to provide the acceleration signal or data derived therefrom for further processing or use.

It should be noted that the wristop computer may without departing from the invention be replaced with any other wearable device, such as another wearable sports tracking unit or a mobile phone capable of communicating with other components of the system.

The means for communicating data between separate devices in a multi-device equipment system typically comprise a wireless radio-frequency transmitter-receiver or transceiver-transceiver pair. The wireless communication protocol can be one used for communication between computers, and/or between any remote sensors, such as a Bluetooth LE or the proprietary ANT+ protocol. These are using direct-sequence spread spectrum (DSSS) modulation techniques and an adaptive isochronous network configuration, respectively. Enabling descriptions of necessary hardware for various implementations for wireless links are available e.g. from the Texas Instrumentt's handbook "Wireless Connectivity" which includes IC circuits and related hardware configurations for protocols working in sub-1- and 2.4-GHz frequency bands, such as ANT™, Bluetooth®, Bluetooth® low energy, RFID/NFC, PurePath™ Wireless audio, ZigBee®, IEEE 802.15.4, ZigBee RF4CE, 6LoWPAN, Wi-Fi®.

As will be described in more detail below, the signal processing and algorithm computing functionalities can be implemented at various levels of the system, e.g. centralized in one device, or distributed between two or more devices. Exemplary system configurations are on a general level listed roughly below, from more centralized to more distributed ones, and may include the following:

ECG and acceleration measurement using sensors in the heart rate belt or smart garment; type of sports determination and energy consumption algorithm processing in a processing unit contained also in the heart rate belt or smart garment; and a completed heart rate and/or energy consumption value being transferable to a second wearable device.

ECG and acceleration measurement using sensors in the heart rate belt or smart garment; type of sports determination being made in the heart rate belt or smart garment; type of sports and relevant data for running the energy consumption algorithm only being transferred to and processed in a second wearable device; and where part of the energy consumption algorithm may be processed in the heart rate belt or smart garment, and part in the second device.

ECG measurement using a sensor in the heart rate belt or smart garment, ECG data being transferred to a second device; acceleration measurement and type of sports being determined in the second wearable device, which also processes the energy consumption algorithm.

The same as above but with acceleration measurement in a third wearable device and acceleration data being transferred to the second wearable device, where the type of sports is determined and the algorithm is processed.

Also combinations of the abovementioned examples and other configurations are available.

Figure 3A:
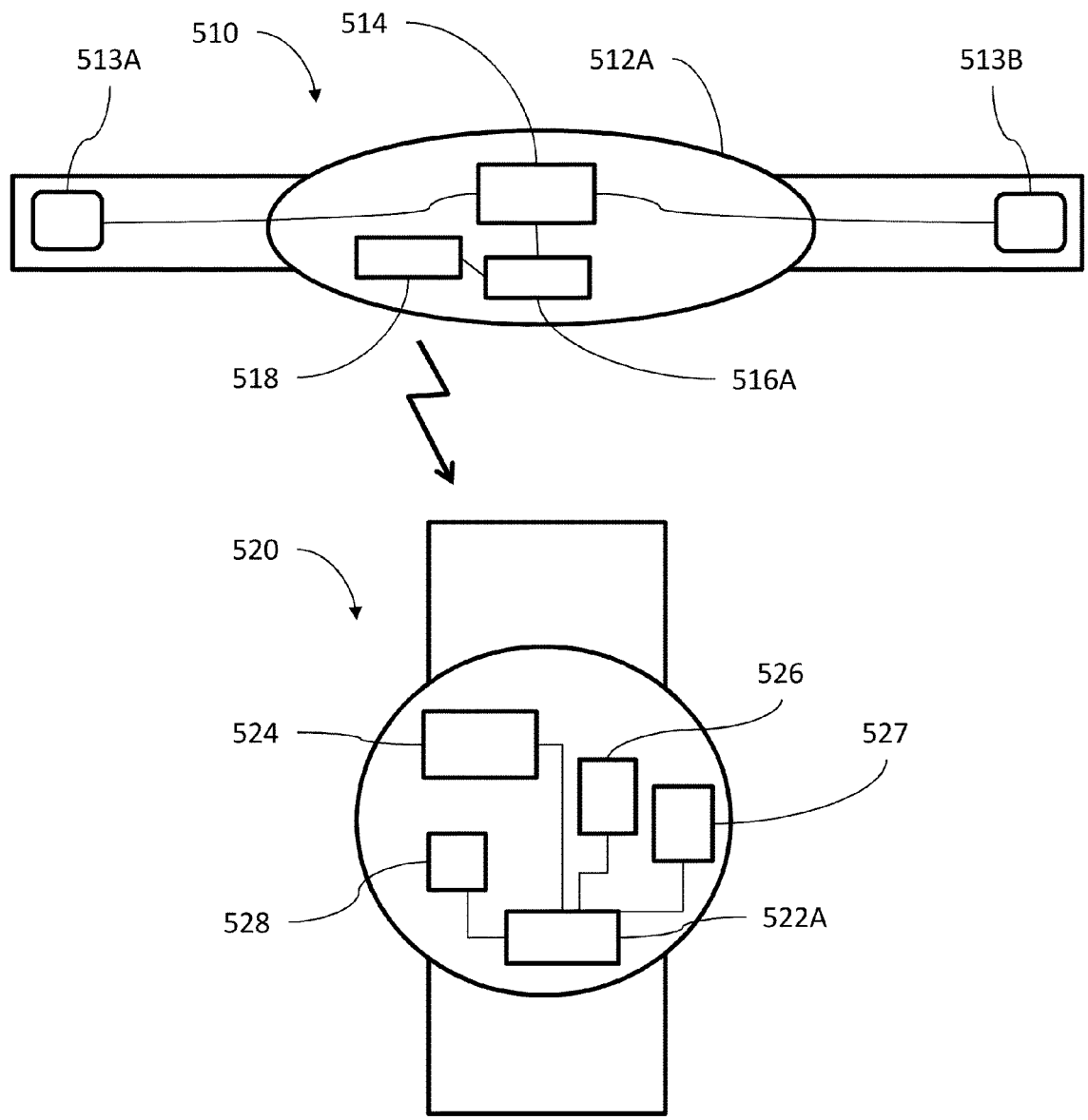
FIG. 3A shows a block diagram of a heart rate belt and a wristop device according to one embodiment of the invention.

FIG. 3A depicts one preferred implementation of the system in more detail. There is provided a heart rate belt 510 with a pair of ECG electrodes 513A, 513B connected to an ECG signal preprocessor 514 (typically including at least an A/D converter) contained in an integral or removable electronics module 512A. The ECG data obtained from the preprocessor is processed in digital form in a processing unit 516A running an algorithm for finding the individual heartbeats and optionally further the heart rate. The heartbeat or the heart rate are wirelessly communicated to a wristop computer 520 via a radio transmitter unit 518 in the belt 510 and radio receiver unit 524 in the wristop computer. The receiver unit 524 is functionally connected to a processing unit 522A. In addition, there is in the wristop computer provided an acceleration sensor 528 functionally connected to the processing unit 522A.

The processing unit 522A is configured to execute a software designed, based on acceleration signals, to determine the type of sports in question. The processing unit is also configured to use algorithms to determine the energy consumption and source(s) of information (ECG and/or acceleration), depending on the sports type determined. Alternatively or in addition to automatic sports type determination, the processing unit may be configured to read a stored parameter indicating the sports type, typically entered by the user or previously automatically determined. The parameter may in the latter case be read from a memory (not shown) of the device and used for selecting an appropriate algorithm and source(s) of information. Exemplary methods for automatic determination of the sports type are described elsewhere in this document.

Figure 3B:
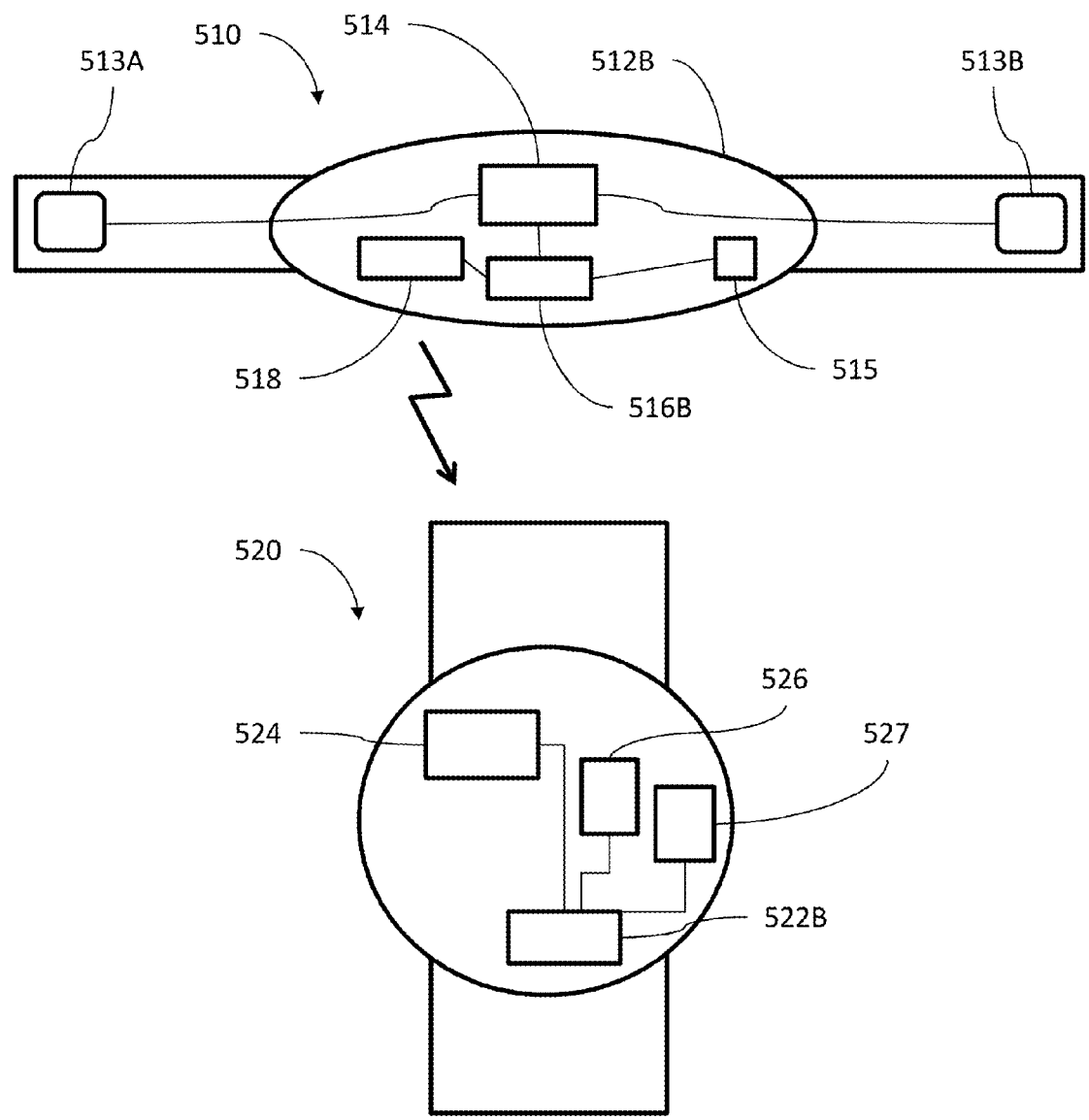
FIG. 3B shows a block diagram of a heart rate belt and a wristop device according to an alternative embodiment of the invention.

FIG. 3B shows an embodiment mostly similar to that of FIG. 3A, but having an acceleration sensor 515 in the electronics module 512B of the heart rate belt. The processing unit 516B is configured to read the acceleration signal from the acceleration sensor 515. According to a first variant, the processing unit 516B is also configured to determine the sports type and to communicate the type, along with the ECG and/or acceleration data, to the wristop computer, which then runs the energy consumption algorithm in its processing unit 522B. According to a second variant, the processing unit 516B of the heart rate belt 510 is also configured to run the energy consumption algorithm either partially or entirely. As an example of partial calculation, energy consumption per mass unit can be determined based on the heartbeat data or acceleration data in the heart rate belt. This is then multiplied with the user mass in the wristop computer through an interface used for entering the mass of the user. In one embodiment, the communication interface between the devices allows for transmission of data to the heart rate belt, whereby also the mass information can be sent and utilized in the heat rate belt to obtain a user-specific energy consumption value.

Figure 4A:
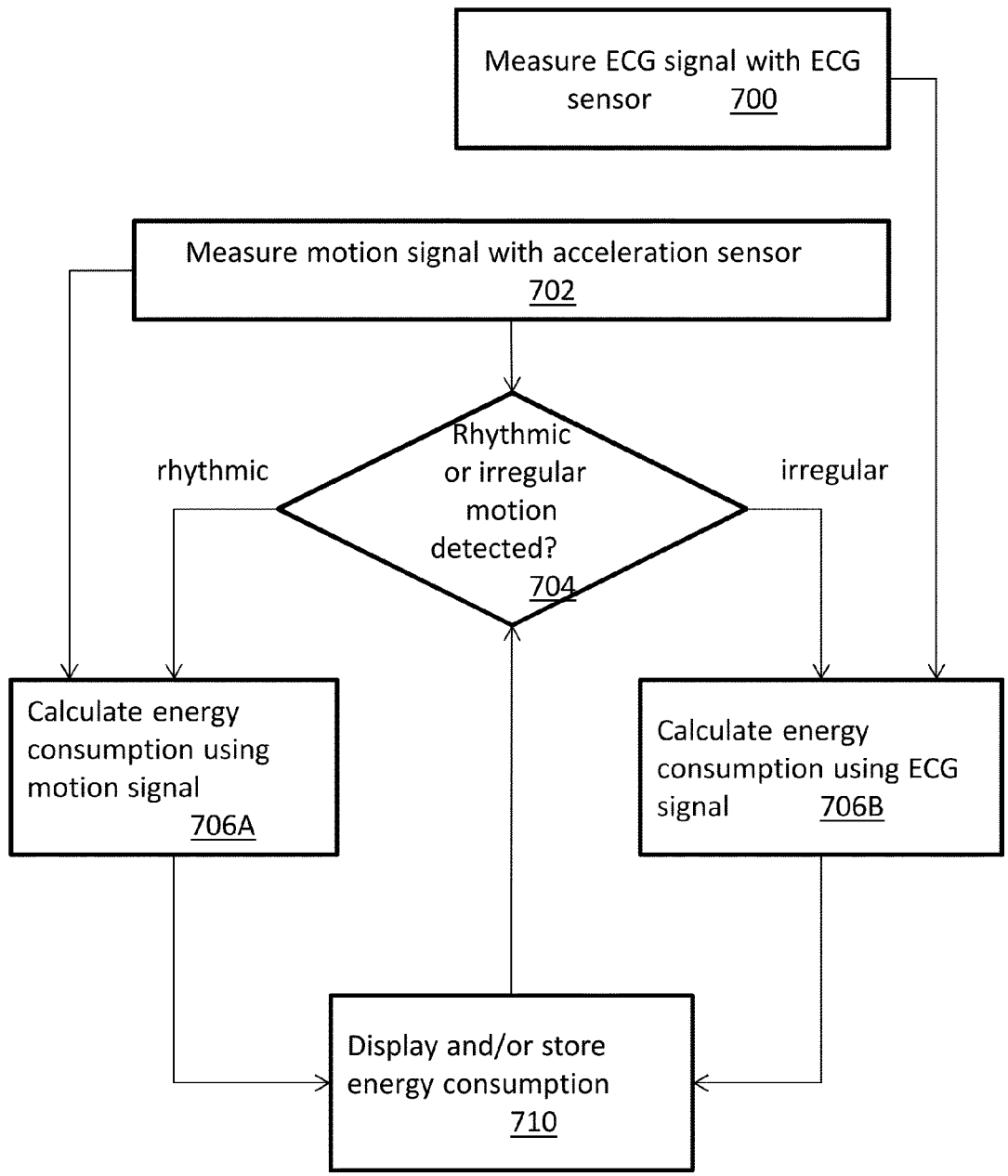
FIG. 4A shows a flow chart of the method according to one embodiment of the invention.

FIG. 4A shows one embodiment of the present method as a flow chart independent of which device each of the steps is carried out in. In step 702, the motion signal is continuously measured with the acceleration sensor (or other motion sensor). Next, in step 704 the motion signal is analyzed so as to detect cyclic, i.e. regular, motion that is characteristic of cyclic sports, such as running Rhythmicity can be determined in the time domain for example by time stamping impulses detected in the signal and by using correlation analysis to determine whether the inter-impulse interval remains constant (to a predefined degree) over time, which would be indicative of a performance of regular nature. If the correlation between intervals is low, the performance is irregular as to its motion pattern. In an alternative embodiment, the acceleration signal is converted to the frequency domain using a discrete Fourier transformation, whereby the presence of strong (peaked) frequency components are detectable. The frequency data will show a peak where a lot of cyclic motion takes place at constant frequency over a chosen time interval. Next, depending on the outcome of the rhythmicity analysis, the energy consumption is calculated either based on the acceleration signal in step 706A, or the heartbeat signal in step 706B. In the latter case, data from the ECG sensor obtained in a continuous measuring step 700 is used, whereas in the former case the acceleration data already used in step 704 is used. In step 710, the energy consumption (and optionally also desired data derived from the acceleration and/or heartbeat signals) is stored in a memory and/or visualized on the display of at least one device. The rhythmicity determination may be carried out continuously or repeated at predefined intervals during the performance, so that the energy consumption algorithm can be changed if the type of sports changes. This can occur for example if the user carries out gymnastic exercises every now and then during a jog.

Energy consumption can be determined starting from the acceleration signal by further utilizing the fact that cadence changes are proportional to the speed of the person, and/or by estimating the speed of the person based on the acceleration data. For example, when walking (<6 km/h) the cadence changes typically between 50 and 70 l/s, in jogging (6-8 km/h) the change is between 70 and 80 l/s, and in running (>8 km/h) between 80 and 90 l/s, depending on the speed. An integral function of acceleration data measured over a time period has also a relation to speed. A mathematical combination of these estimates gives a good overall estimate on the speed of the person. When the speed is known, one can estimate VO2 and further the energy consumption. Expressed mathematically, energy consumption can be estimated using a formula $A*Cd*\Sigma a+B$, where Cd is cadence, $\Sigma a$ is the abovementioned integral and A and B are personal calibration factors.

Figure 4B:
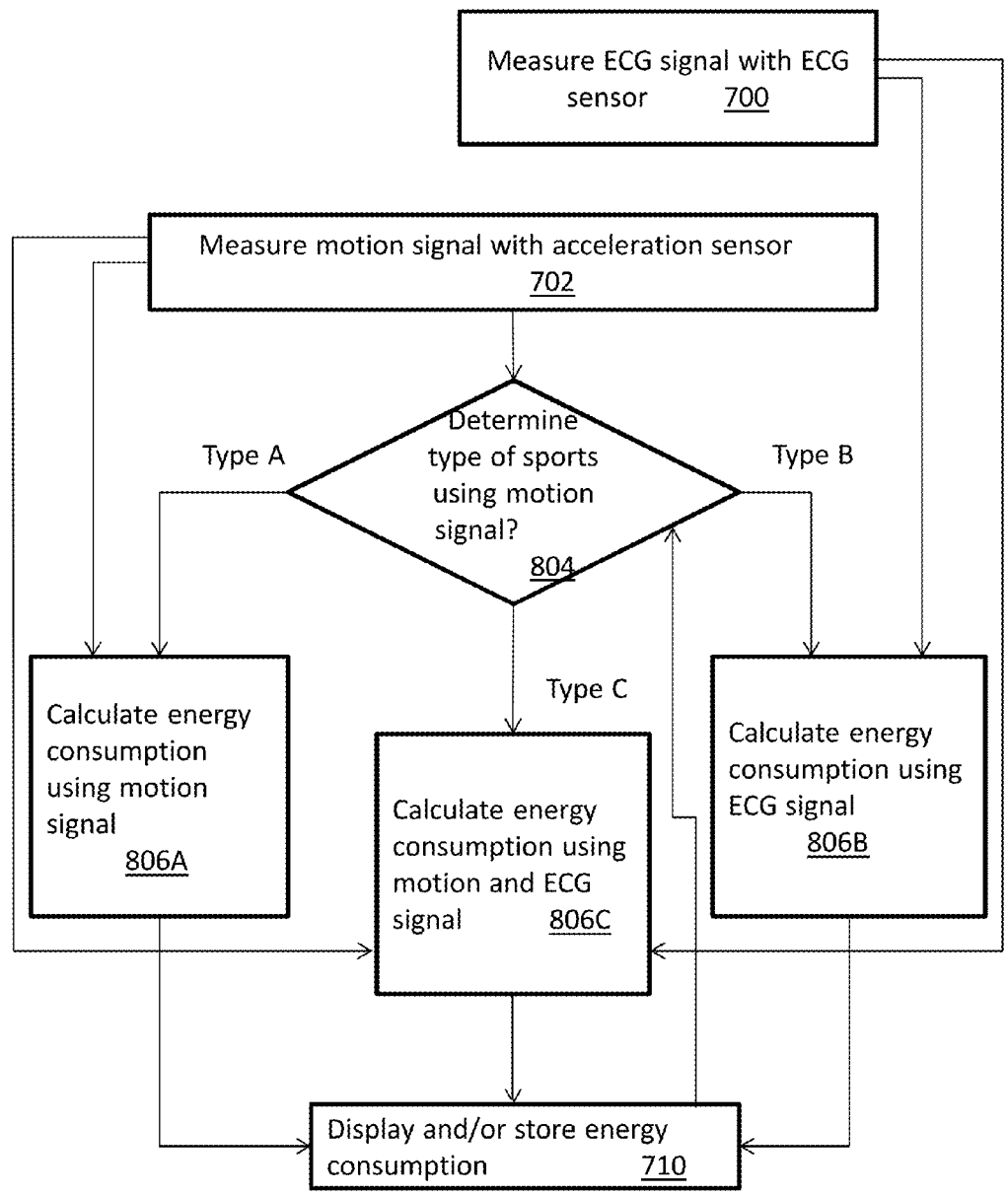
FIG. 4B shows a flow chart of the method according to an alternative embodiment of the invention.

FIG. 4B shows a variant which is otherwise similar to the method of FIG. 4A, but having the capability to distinguish between three type of sports in the determination step 804. If a type A is detected, energy consumption is calculated using motion signal in step 806A. The ECG signal is used in step 806B if type B is detected. In the case of type C, the energy consumption is calculated on the basis of both signals in combination, or other data such as a satellite positioning (or other data yielding the speed of the person) data in step 806C. To give an example, type A may be suitable for running, type B suitable for tennis and type C suitable for swimming. The energy consumption methods may also be different than those exemplified here. To distinguish between different types of rhythmic sports (such as running, skiing and swimming), the frequency of rhythmic motion and/or multidimensional motion (acceleration) signal analysis may also give information on the particular sports and can be used in some embodiments.

Figure 5:
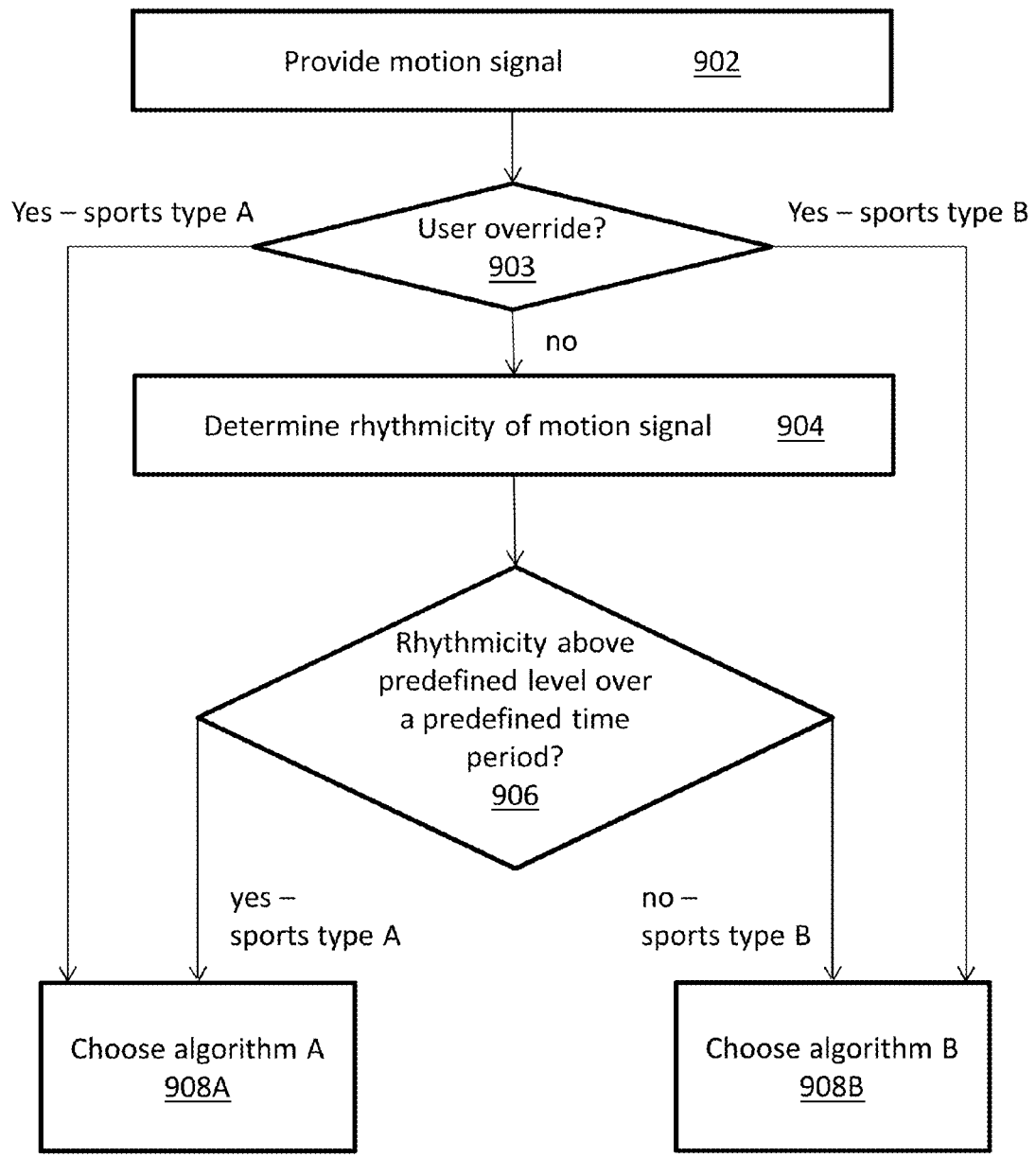
FIG. 5 shows still another flow chart depicting the algorithm choosing phase of the invention in more detail.

FIG. 5 shows in still more details the sports type determination phase according to one embodiment. The motion signal is measured in step 902. Then, in step 903 it is determined if the user has manually specified a particular sports type, and wishes that to be used as a basis for algorithm selection. If affirmative, that algorithm is chosen and overrides the automatic determination (steps 908A and 908B). If negative, automatic type determination is initiated. First, the rhythmicity of the motion signal is determined in step 904 using a suitable method (such as the time stamp method or Fourier method described above). Next, in phase 906 it is checked whether the rhythmicity is above or below a predefined rhythmicity threshold level. Phases 904 and 906 should be carried out over a time period of significant length so that random and occasional variations in the frequency of motion, or measurement errors, do not result in a wrong outcome. If the rhythmicity stays relatively constant over the period chosen, a first algorithm is chosen for further calculations and on the opposite case a second algorithm is chosen (steps 908A and 908B).

Irrespective of whether cadence, heart rate, speed, or any combination of these, is used for determination of energy consumption, also other measurement data, such as ascent or descent speed obtained from a suitable sensor (e.g. satellite positioning sensor or barometer), can be taken into account and used as a corrective factor to get a more accurate estimate of the energy consumption.

It is to be understood that the embodiments of the invention disclosed are not limited to the particular process steps, units, components, devices, materials or products disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, various embodiments and examples of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the description, numerous specific details are provided, such as examples of shapes and dimensions etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. Wearable electronic equipment for monitoring a sports performance of a person, comprising:
    means for reading a heartbeat signal corresponding to heartbeat of the person during the performance,
    means for reading a motion signal corresponding to motion of the person during the performance,
    means for calculating an energy consumption parameter using one or more of said signals, and
    means for determining a type of the sports performance
wherein:
    the means for determining the type of the sports performance are adapted to calculate a parameter depicting the rhythmicity of the performance based on said motion signal, and
    the means for calculating the energy consumption parameter are adapted to utilize the heartbeat signal if the rhythmicity of the performance is below a predefined level and to utilize the motion signal if the rhythmicity of the performance is above a predefined level.

2. The wearable electronic equipment according to claim 1, further comprising means for receiving and storing a user-specified sports performance type parameter in a memory of the equipment which can be read by the means for determining the type of the sports performance in order to determine the type of the sports performance.

3. The wearable electronic equipment according to claim 1, wherein the means for determining the type of the sports performance are adapted to determine the type of the sports performance automatically based on characteristics of the motion signal.

4. The wearable electronics equipment according to claim 1, wherein the means for determining the type of the sports performance are adapted to determine rhythmicity of the motion signal by:
    detecting repeating features in the motion signal,
    associating time stamps to the repeating features, and
    determining any correlation between intervals between successive time stamps.

5. The wearable electronics equipment according to claim 1, wherein the means for determining the type of the sports performance are adapted to apply Fourier analysis to the motion signal in order to determine the rhythmicity of said motion signal.

6. The wearable electronic equipment according to claim 1, further comprising an electronic module having an acceleration sensor for providing said motion signal, and a heart rate belt or smart garment with ECG measurement electrodes for providing said heartbeat signal, and wherein said heart rate belt or smart garment is integral or connectable with said electronic module.

7. The wearable electronic equipment according to claim 6, further comprising in said electronics module:
    means for calculating the energy consumption parameter based on at least one of: the heartbeat signal and motion signal, depending on the type of sports performance determined, and
    means for wirelessly communicating the energy consumption parameters to another electronic device.

8. The wearable electronic equipment according to claim 1, wherein said means for calculating the energy consumption parameter are adapted to estimate at least on of a cadence and speed of the person on the basis of a motion signal and to derive the energy consumption parameter using at least one of an estimated cadence and speed.

9. The wearable electronic equipment according to claim 1, further comprising a displayless device comprising at least said means for reading the heartbeat signal.

10. The wearable electronic equipment according to claim 1, futher comprising a wristop computer or mobile phone, whereby said means for reading the heartbeat signal are adapted to receive the signal(s) wirelessly from a separate measurement device.

11. The wearable electronic equipment according to claim 1, wherein the energy consumption parameter is provided in the units of energy consumption per mass unit of a person or total energy consumption of said person.

12. The wearable electronic equipment according to claim 1, wherein said means for reading a heartbeat signal comprise one or more electrical ECG sensors, optical sensors, pressure sensors or acceleration sensors.

13. The wearable electronic equipment according to claim 12, wherein the one or more sensors is/are adapted to be positioned against the chest, neck, wrist or auricle of the person during the performance.

14. A method for monitoring a sports performance of a person, comprising:
- providing a heartbeat signal corresponding to heartbeat of the person during a performance,
- providing a motion signal corresponding to motion of the person during said performance,
- calculating an energy consumption parameter using one or more of said signals, and
- determining the type of sports of said performance, wherein
- determining the type of the sports performance is carried out by calculating a rhythmicity parameter based on said motion signal,
- calculating the energy consumption parameter by using the motion signal for calculating the energy consumption parameter if the rhythmicity parameter is above a predefined level and using the heartbeat signal for calculating the energy consumption parameter if the rhythmicity parameter is below the predefined level, and
- said heartbeat signal and said motion signal are measured, and the type of the sports performance is determined, in an electronic module located in or mountable to a wearable device.

15. The method according to claim 14, wherein said determining of the type of the sports performance is carried out by reading a user-specified sports type parameter entered via a user interface.

16. The method according to claim 14, wherein said determining of the type of the sports performance is carried out automatically based on characteristics of the motion signal.

* * * * *